US006781697B1

(12) United States Patent
Carra et al.

(10) Patent No.: US 6,781,697 B1
(45) Date of Patent: Aug. 24, 2004

(54) PORTABLE SYSTEM AND METHOD FOR DETERMINING ONE OR MORE REFLECTANCE PROPERTIES OF A SURFACE

(75) Inventors: William M. Carra, Fort Worth, TX (US); Russell G. Torti, Arlington, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 129 days.

(21) Appl. No.: 10/052,200

(22) Filed: Jan. 16, 2002

(51) Int. Cl.[7] .............................................. G01N 21/47
(52) U.S. Cl. ...................................... 356/446; 356/236
(58) Field of Search ..................... 356/236, 445–448, 356/600, 237.2, 237.1; 250/228

(56) References Cited

U.S. PATENT DOCUMENTS

| | | | |
|---|---|---|---|
| 2,515,762 A | | 7/1950 | Dimmick ........................ 88/14 |
| 4,360,275 A | * | 11/1982 | Louderback ................. 356/446 |
| 4,569,594 A | | 2/1986 | Cabi-Akman et al. ....... 356/408 |
| 4,655,225 A | * | 4/1987 | Dahne et al. ................ 600/316 |
| 5,098,187 A | * | 3/1992 | Judge .......................... 250/228 |
| 5,659,397 A | | 8/1997 | Miller et al. ................. 356/446 |
| 5,828,460 A | * | 10/1998 | Lucovsky et al. ........... 356/446 |
| 6,201,601 B1 | * | 3/2001 | Vaez-Iravani et al. ... 356/237.4 |

FOREIGN PATENT DOCUMENTS

| | | | |
|---|---|---|---|
| EP | 0 655 620 A1 | 5/1995 | ........... G01N/21/47 |
| EP | 0 987 540 A2 | 3/2000 | ........... G01N/21/64 |

OTHER PUBLICATIONS

Author: B. Rajan, "Operators Manual for Reflectometer (16RU3000–1)", Lockheed Martin Tactical Aircraft Systems, 21 pages, Oct. 17, 1994.

International Search Report in International Application Serial No. PCT/US 03/00561 dated Feb. 10, 2004, 8 pages, Feb. 10, 2004.

International Search Report in International Application No. PCT/US 03/00561, dated Nov. 7, 2003, 5 pages, Nov. 7, 2003.

* cited by examiner

*Primary Examiner*—Richard A. Rosenberger
(74) *Attorney, Agent, or Firm*—Baker Botts L.L.P.

(57) ABSTRACT

A method is provided for determining one or more reflectance properties of a surface using a portable apparatus that includes reflecting a first beam of electromagnetic energy off of a measured surface, the first beam contacting the measured surface at an angle that is near normal to the measured surface. The method also includes reflecting a second beam of electromagnetic energy off of the measured surface, the second beam contacting the measured surface at an angle that is near grazing to the measured surface. Reflected portions of the first and second beams of electromagnetic energy are then collected and at least one reflectance characteristic value associated with the measured surface is determined based on the reflected portions of the first and second beams of electromagnetic energy.

68 Claims, 5 Drawing Sheets

PORTABLE SYSTEM AND METHOD FOR DETERMINING ONE OR MORE REFLECTANCE PROPERTIES OF A SURFACE

TECHNICAL FIELD OF THE INVENTION

This invention relates in general to reflectance determination and, more particularly, to a portable system and method for determining one or more reflectance properties of a surface.

BACKGROUND OF THE INVENTION

The ability to accurately evaluate reflectance properties of an object or a surface has become increasingly important. Reflectance properties may, for example, influence radar measurements or other visibility characteristics of an aircraft or other object. One problem associated with reflectance measurement systems is the inability to obtain reflectance property values quickly and accurately. In addition, reflectance measurement systems generally lack flexibility in adapting to various environments as the measurement systems are generally stationary laboratory instruments, which preclude in-situ measurements of an object or a surface.

SUMMARY OF THE INVENTION

The present invention provides a system and method for determining one or more reflectance properties of a surface that substantially reduce or eliminate problems and disadvantages associated with the previous systems and methods.

In a particular embodiment, the present invention provides a method for determining one or more reflectance properties of a surface using a portable apparatus that includes reflecting a first beam of electromagnetic energy off of a measured surface, the first beam contacting the measured surface at an angle that is near normal to the measured surface. The method also includes reflecting a second beam of electromagnetic energy off of the measured surface, the second beam contacting the measured surface at an angle that is near grazing to the measured surface. Reflected portions of the first and second beams of electromagnetic energy are then collected and at least one reflectance characteristic value associated with the measured surface is determined based on the reflected portions of the first and second beams of electromagnetic energy.

In accordance with another embodiment, an electromagnetic energy controller is provided for a portable measuring apparatus that comprises a chopper operable to transmit a first portion of electromagnetic energy toward a first reflecting element and to reflect a second portion of electromagnetic energy toward a second reflecting element and to absorb a third portion of electromagnetic energy. The chopper executes a repetitive cycle in which the chopper transmits, reflects, and then absorbs portions of electromagnetic energy. The first and second portions of electromagnetic energy are reflected by the first and second reflecting elements respectively toward a surface plane. An integrator receives reflected electromagnetic energy from the surface plane that is communicated to a processor, the processor being coupled to the integrator and being operable to determine a reflectance characteristic associated with the surface plane that is based on the reflected electromagnetic energy from the surface plane. The electromagnetic energy controller also includes a motor provided to effect motion of the chopper.

Technical advantages of the present invention include providing an instrument that is portable and that measures at least one reflectance characteristic of a surface. This would allow, for example, a user of the portable measurement instrument to determine a reflectance characteristic of an object or element in-situ, i.e. without having to remove or otherwise displace the object or element from its natural environment. This could be particularly beneficial in the field of aeronautics where the surface of an aircraft, for example, would yield a reflectance characteristic as determined by the portable measuring instrument while remaining in place. This avoids the dilemma of having to remove a component (or alternatively, having to cut out a sample of the component), such as a wing of an aircraft for example, and positioning the component in a laboratory in order to determine its reflectance characteristics.

Another technical advantage of one embodiment of the present invention is increased accuracy in calculating a reflectance characteristic for an object or element. This is due, in part, to the utilization of multiple angles of incidence being nearly simultaneously reflected at a surface to which reflectance characteristics are sought to be determined. In addition, each angle of incidence has an associated set of frequency bands that operate to provide measurements at four designated frequency ranges within the frequency spectrum. As a result, the portable measuring system of the present invention operates to provide at least eight measurements that may be averaged, synthesized or otherwise processed in order to offer a highly accurate measurement associated with at least one reflectance characteristic of a surface.

Still another technical advantage of one embodiment of the present invention is the use of a chopper that comprises an absorptive portion that provides calibration to the portable measuring system. The absorptive portion absorbs electromagnetic energy and provides a constant point of reference to detectors that measure electromagnetic energy levels as reflected from the surface. These detectors may provide immediate feedback to a processor. The processor may then process the data associated with the absorbed electromagnetic energy and accordingly modify a calibration parameter associated with the portable measuring device. This may in turn result in increased accuracy of the system, while still maintaining a high level of speed in operation of the instrument. This would allow, for example, an operator of the reflectance determination system to quickly and accurately evaluate one or more reflectance properties associated with a given surface and establish whether or not maintenance is required on the surface (or alternatively, that maintenance has been performed adequately on the surface, i.e., within a designated specification).

Embodiments of the present invention, which follow, may enjoy some, all, or none of these advantages. Other technical advantages of the present invention are readily apparent to one skilled in the art from the following figures, the description and the claims.

BRIEF DESCRIPTION OF THE DRAWINGS

For a more complete understanding of the present invention and its advantages, reference is now made to the following description taken in conjunction with the accompanying drawings, wherein like numerals represent like parts, in which.

DETAILED DESCRIPTION

Example embodiments of the present invention are best understood by referring now to FIGS. 1 through 5 of the drawings in which like numerals refer to like parts.

Figure 1:
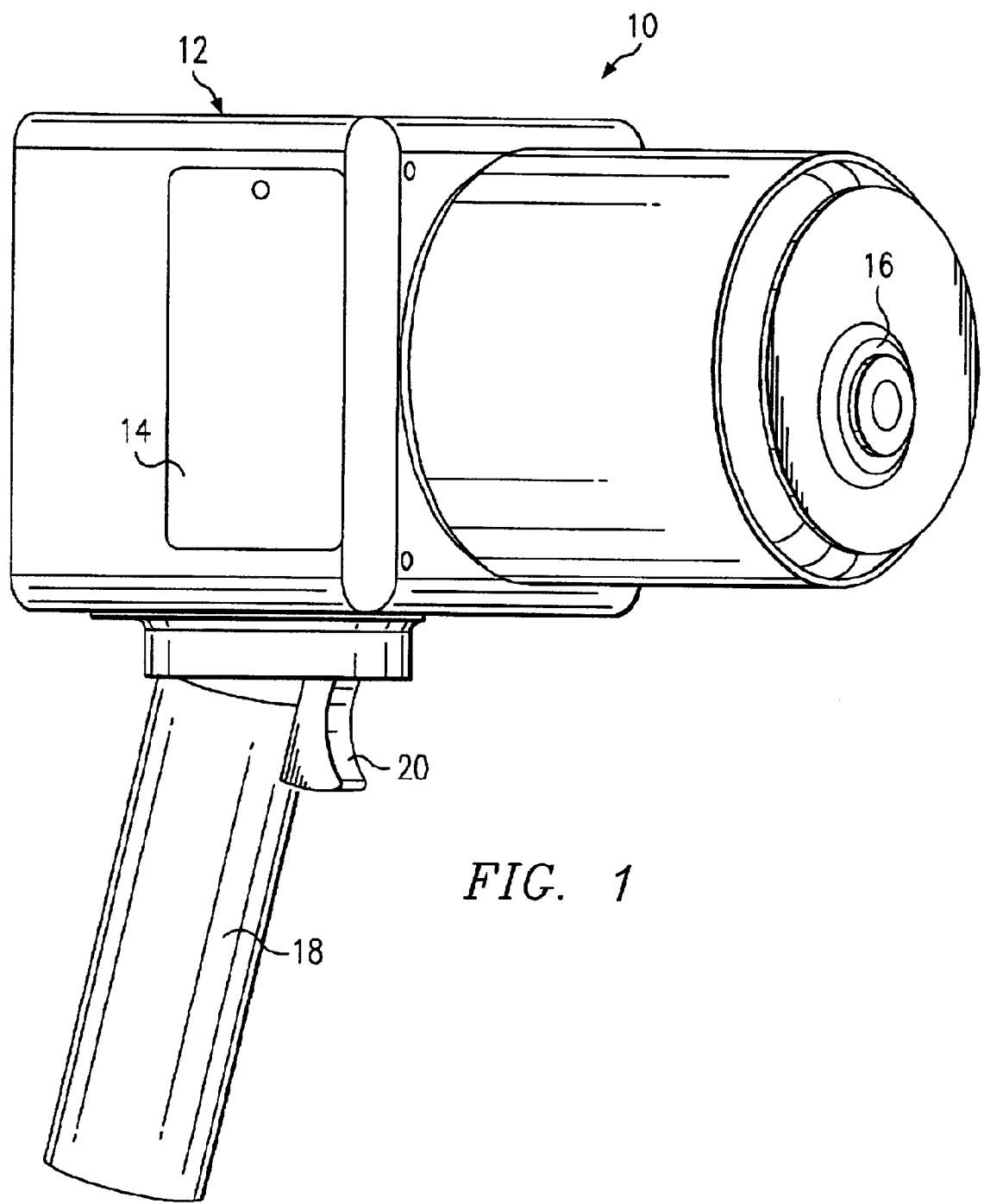
FIG. 1 is a perspective diagram illustrating a portable reflectance determination system in accordance with one embodiment of the present invention.

FIG. 1 illustrates a reflectance determination system 10 in accordance with one embodiment of the present invention. In this embodiment, reflectance determination system 10 is a hand-held portable device. Reflectance determination system 10 is generally portable, portable in that it can be carried or otherwise moved to a test surface and can be used in normal operation in any one of a number of environments. Reflectance determination system 10 may otherwise be suitably configured where appropriate according to particular needs.

Reflectance determination system 10 comprises a housing 12 that includes a battery compartment 14 and a measurement port 16 for communicating electromagnetic energy. Reflectance determination system 10 also comprises a handle 18 and a trigger 20. Housing 12 provides a protective barrier to the internal structure of reflectance determination system 10. Battery compartment 14 provides access to a battery or other suitable power source included within housing 12.

Measurement port 16 provides a communication link for electromagnetic energy that may be transmitted to and received from a measured, or target surface. The target surface may be flat or curved, convex or concave, coated or otherwise layered or simply a raw material to which a reflectance or an emissive characteristic or property is sought to be determined. Measurement port 16 may have one or more openings or windows that may be flush with the measured, or target surface. A port interface element 17 is configured to suitably space and align a target surface with reflectance determination system 10 (the measured surface plane is identified in FIG. 3 as a target surface 15 and discussed below with reference thereto). In one embodiment target surface 15 is flush with port interface element 17.

Handle 18 is a generally tubular structure that allows reflectance system 10 to be hand-held and appropriately pointed toward a surface plane to which one or more reflectance characteristics are sought to be determined. Trigger 20 may provide an initiation element or mechanism for the operation of reflectance determination system 10 in activating or otherwise triggering a power source, for example.

In operation, reflectance determination system 10 generates electromagnetic energy that is communicated via measurement port 16 and to a target surf ace to which one or more reflectance characteristics are sought to be determined. Reflectance characteristics as used herein in this document refers to any reflectance or emissive property, factor, attribute or quality of a surface or material. Reflectance determination system 10 further provides a portable instrument that gathers information or data relating to one or more reflectance characteristics based on multiple angles of incidence. In addition, internal structure or elements (to be discussed in greater detail with reference to FIGS. 2 through 4) are provided within housing 12 that operate to simultaneously recognize electromagnetic energy from multiple frequency bands within the frequency spectrum per angle of incidence. With the use of multiple frequency bands and multiple angles of incidence, reflectance determination system 10 achieves a high level of accuracy in determining a reflectance characteristic of a target surface. In addition, the present invention offers the ability to evaluate multiple wavelengths simultaneously without requiring a physical changing out of components, such as frequency filters for example, in order to identify electromagnetic energy from various bands within the frequency spectrum.

Moreover, because of the portable nature of reflectance determination system 10, reflectance measurements may be made in virtually any environment where reflectance determination system 10 may be suitably positioned. This would allow reflectance determination system 10 to evaluate a wide number of flat or shaped surfaces in-situ, i.e., without having to alter or otherwise remove the surface to which a reflectance determination is sought. In addition, reflectance determination system is light-weight, approximately 2 lbs. in a particular embodiment of the present invention, allowing an operator to both carry and to manipulate the instrument with minimal effort.

Figure 2:
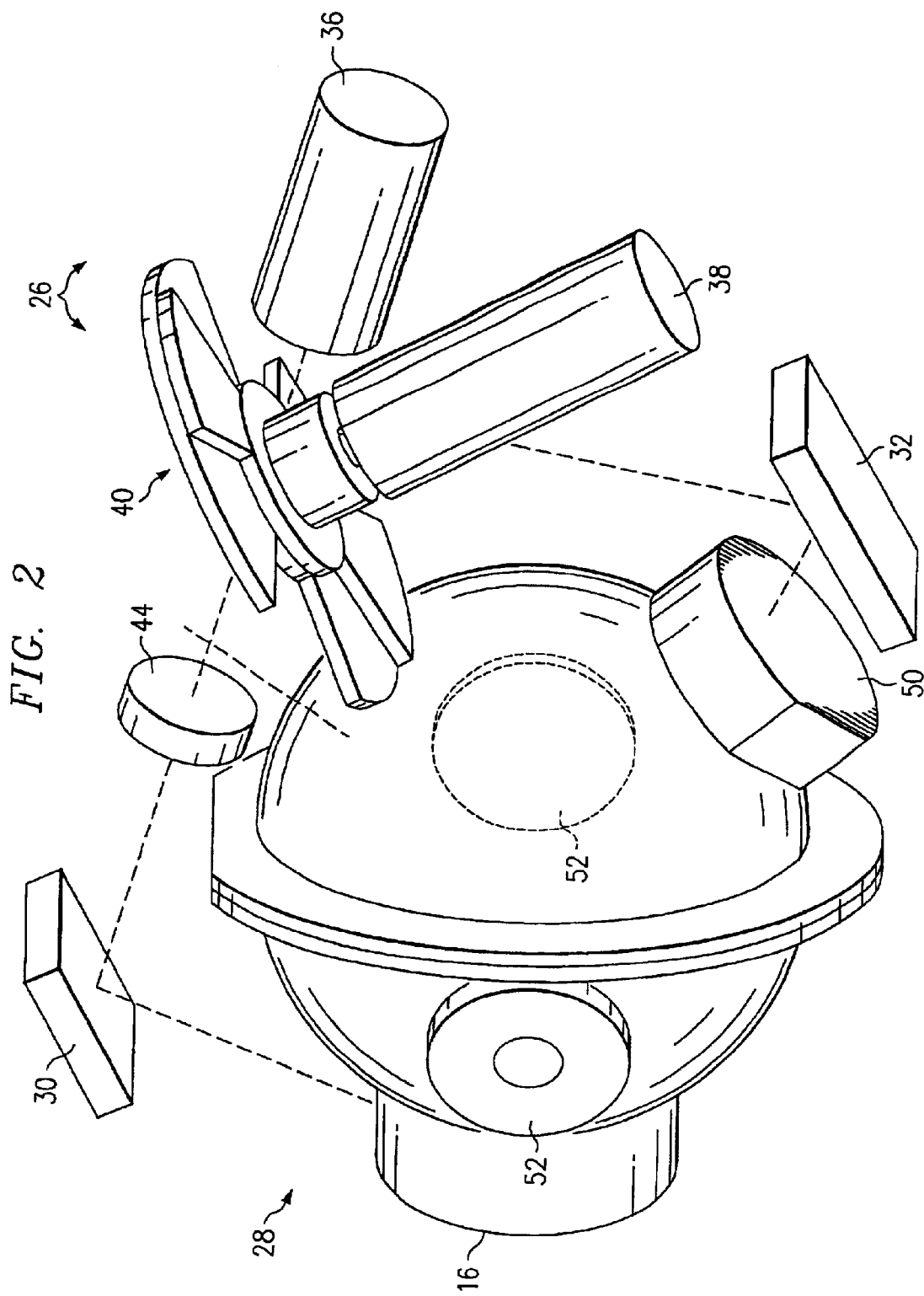
FIG. 2 is a perspective diagram illustrating internal elements of the reflectance determination system of FIG. 1 in accordance with one embodiment of the present invention.

Turning to FIG. 2, FIG. 2 illustrates internal elements of reflectance determination system 10 in accordance with one embodiment of the present invention. In a particular embodiment, FIG. 2 represents a series of elements provided within housing 12, housing 12 having been rotated slightly in FIG. 2.

Reflectance determination system 10 comprises an electromagnetic energy system 26, an integrator 28, a first reflecting element 30, and a second reflecting element 32. These internal components cooperate with each other in order to communicate electromagnetic energy toward a target surface to which a reflectance characteristic is sought. In addition, these components cooperate such that reflected electromagnetic energy from target surface 15 (as identified in FIG. 3) may be collected by reflectance determination system 10 and further processed such that a reflectance characteristic value is obtained.

Electromagnetic energy system 26 comprises an energy source 36, a motor 38, and a chopper 40. Electromagnetic energy system 26 operates generally to supply and to direct electromagnetic energy to first reflecting element 30 and second reflecting element 32. Electromagnetic energy system 26 may also be referred to as an electromagnetic energy controller herein, providing a unit that generates and influences electromagnetic energy within reflectance determination system 10.

According to one embodiment of the present invention, energy source 36 generates infrared energy to be communicated to chopper 40. Energy source 36 may comprise an infrared lamp operable to generate a collimated beam of broadband infrared light to be communicated to chopper 40. Alternatively, energy source 36 may generate any other suitable electromagnetic energy that is communicated to chopper 40. Although described as inclusive of a single energy source 36, electromagnetic energy system 26 may alternatively include multiple energy sources where appropriate, the energy sources being operable to provide electromagnetic energy to reflectance determination system 10.

Energy source 36 is always ON in a particular embodiment of the present invention, providing stability via an internal thermal equilibrium. Alternatively, energy source 36 may be powered up or down by an operator of reflectance determination system 10 or a program, routine or algorithm within housing 12. Energy source 36 is positioned such that the electromagnetic energy that it generates propagates toward chopper 40 at an angle of approximately 45° as measured from the central axis of chopper 40 (illustrated in greater detail in FIG. 3 as angle θ). Although illustrated as generating electromagnetic energy propagating toward chopper 40 at an angle of 45°, energy source 36 may be positioned at any suitable angle where appropriate such that electromagnetic energy suitably propagates toward chopper 40.

Motor 38 provides a drive element for chopper 40 according to one embodiment of the present invention. Motor 38 is coupled to chopper 40 and generates motion of one or more rotating chopper discs of chopper 40 (as described in more detail below with reference to the discussion involving chopper 40). Motor 38 may be any suitable driving mechanism or element operable to effect motion of chopper 40 generally. Motor 38 may be powered by a battery or by any other suitable power source operable to provide the requisite energy to effect motion of the discs of chopper 40.

Chopper 40 comprises two rotating discs at one end that operate to reflect, to pass, and to absorb electromagnetic energy provided by energy source 36 according to the teachings of a particular embodiment of the present invention. Chopper 40 may comprise a partial disc or a plurality of suitable discs where appropriate. Alternatively, chopper 40 may comprise any object or element (having any suitable shape or form) operable to facilitate the communication of electromagnetic energy to first reflecting element 30 and/or second reflecting element 32. In one embodiment in which multiple energy sources are provided, chopper 40 may be eliminated entirely.

A portion of the spinning discs of chopper 40 are transmissive and thus accordingly transmit electromagnetic energy to first reflecting element 30 when the transmissive portion(s) of the rotating discs coincide with a path of propagation of electromagnetic energy generated by energy source 36. In a particular embodiment of the present invention, chopper 40 comprises multiple discs that include portions, which define absent sections or cavities that allow electromagnetic energy from energy source 36 to pass directly to first reflecting element 30. This absence of structure within chopper 40 provides an unaffected beam of electromagnetic energy that propagates toward first reflecting element 30. Alternatively, the transmissive portion of chopper 40 may comprise glass or any other suitable material operable to pass a portion of electromagnetic energy therethrough. In addition, the transmissive portion of chopper 40 may include a coating that operates to pass a portion of electromagnetic energy.

Chopper 40 also comprises a reflective portion within one or more of the spinning discs. The reflective portion is gold-plated aluminum (Al) in one embodiment, that reflects a portion of electromagnetic energy generated by energy source 36 to second reflecting element 32. Alternatively, the reflective portion of chopper 40 may comprise any suitable material or coating operable to reflect at least a portion of electromagnetic energy propagating from energy source 36. As illustrated in more detail in FIG. 3, the reflective portion of chopper 40 directs electromagnetic energy from energy source 36 toward second reflecting element 32 at an angle that is approximately normal, normal as measured from an axis of propagation of energy source 36. Alternatively, the reflective portion of chopper 40 may direct electromagnetic energy received from energy source 36 at any angle or at any direction according to particular needs.

Chopper 40 also comprises an absorptive portion within one or more of the spinning discs that absorb part of the electromagnetic energy generated by energy source 36. According to a particular embodiment of the present invention, the absorptive portions of chopper 40 comprise aluminum (Al), which is treated with a highly absorptive paint. The absorptive portion provides a point of reference for detectors that measure electromagnetic energy levels reflected from target surface 15. Particularly, the absence of electromagnetic energy serves as a point of reference for an element, such as a processor or a detector element for example, that may calibrate one or more parameters associated with electromagnetic energy. This calibration function is described in more detail below with reference to FIG. 4.

Figure 3:
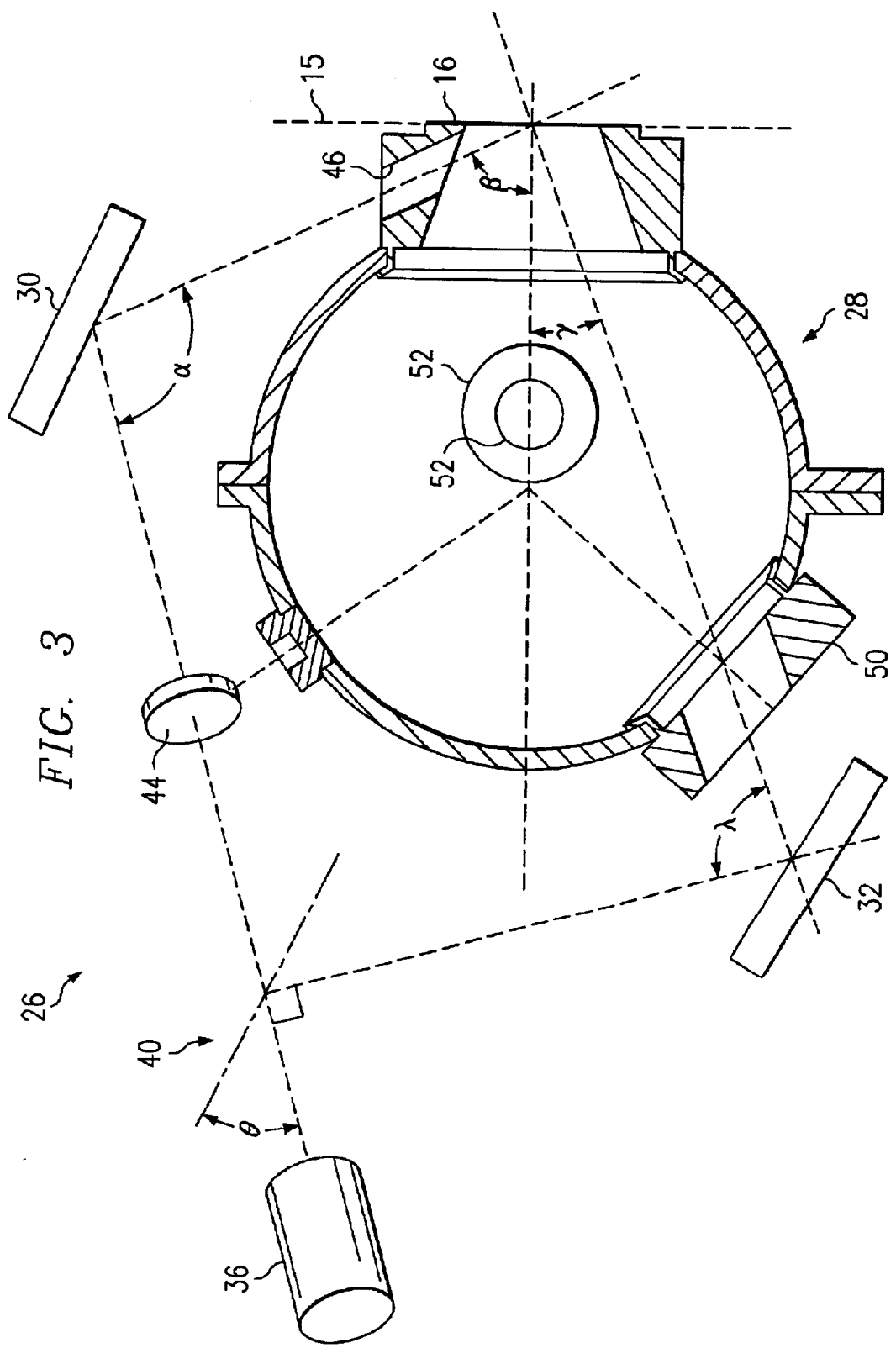
FIG. 3 is a cross-sectional diagram of the internal components of FIG. 2 in accordance with one embodiment of the present invention.

First reflecting element 30 is a mirror that includes a gold surface according to one embodiment of the present invention; however, first reflecting element 30 may be formed of any other suitable material (such as highly-polished aluminum (Al) for example) where appropriate. Electromagnetic energy is directed toward first reflecting element 30 at an angle of approximately 100° as measured from a line of propagation of electromagnetic energy originating from energy source 36. This angle is illustrated in FIG. 3 as α, but alternatively may be any other suitable angle according to particular needs. First reflecting element 30 reflects a portion of electromagnetic energy received from chopper 40 when electromagnetic energy from energy source 36 passes generally through the transmissive portion of the spinning discs of chopper 40. First reflecting element 30 directs a portion of the electromagnetic energy that it receives toward target surface 15, to which a reflectance characteristic is sought to be determined.

According to one embodiment of the present invention, the angle at which this electromagnetic energy is directed by first reflecting element 30 toward target surface 15 is near grazing, i.e. approximately parallel to target surface 15, more specifically greater than 0° and up to approximately 30° with respect to target surface 15. As referred to in the field of optics, the angle of incidence of the electromagnetic energy that is directed towards the surface (as indicated by 'β' in FIG. 3) is the range of approximately 60° to 90° with respect to the normal to target surface 15, such normal as being defined as 90° to target surface 15. Alternatively, first reflecting element 30 may direct electromagnetic energy toward target surface 15 at any suitable angle such that data associated with electromagnetic energy may be collected that relates to the reflectance characteristic of an associated surface plane.

Second reflecting element 32 is also a mirror that comprises a gold surface in one embodiment of the present invention; however, second reflecting element 32 may be formed of any other suitable material (such as highly-polished aluminum (Al) for example) where appropriate. Second reflecting element 32 receives electromagnetic energy when the reflective portion of the spinning discs of chopper 40 cooperate to reflect a portion of electromagnetic energy. Second reflecting element 32 receives a portion of electromagnetic energy from the reflective portion of the spinning discs of chopper 40 and directs that portion of electromagnetic energy toward target surface 15 at an angle approximately normal to target surface 15 to which attitude determination is sought (normal as defined as being from 90° with respect to target surface 15 to variances of 30° in either direction, i.e. at 60° and 90° respectively with respect to target surface 15). This angle is illustrated in FIG. 3 as γ, but may alternatively be any other suitable angle where appropriate such that a portion of electromagnetic energy is directed toward target surface 15. It will be noted that second reflecting element 32 may change the direction of propagation of the electromagnetic energy through an angle of approximately 90°, as indicated by λ in FIG. 3.

First reflecting element 30 and second reflecting element 32 collectively operate to significantly reduce background noise or extraneous electromagnetic energy that may be received via measuring port 16. Such background noise may be particularly problematic in other systems that do not offer more than one angle of incident to evaluate reflectance characteristics or properties of a target surface. In contrast to other systems that only offer a single angle of incident, the present invention reduces the number of errors that are introduced into the system because of the sampling or averaging of electromagnetic energy at two angles, i.e. erroneous results from two measurements may produce a consensus allowing for deletion of values outside of a predetermined range.

A lens 44 may optionally be provided between chopper 40 and first reflecting element 30. Lens 44 focuses a beam of electromagnetic energy communicated by energy source 36 and through chopper 40. Alternatively, the communication pathway between first reflecting element 30 and energy source 36 may include any other suitable focusing, defocusing, amplification, modification or influencing optical element operating to effect the communications therebetween. In addition, such an optical element may be placed in any line of communication within reflectance determination system 10 (such as between energy source 36 and second reflecting element 32) in order to facilitate or otherwise enhance a determination of a reflectance characteristic associated with target surface 15.

Integrator 28 comprises an input port so, measurement port 16, and one or more detectors 52 according to one embodiment of the present invention. In a particular embodiment of the present invention, integrator 28 is an integrating sphere that collects a portion of electromagnetic energy. Alternatively, integrator 28 may be any shape or size and additionally include any component, object or element operable to facilitate the communications of electromagnetic energy. In one embodiment of the present invention, integrator 28 operates to both receive reflected electromagnetic energy from and transmit electromagnetic energy to target surface 15.

Input port 50 is coupled to integrator 28 in a particular embodiment of the present invention, but alternatively may be included within integrator 28 or provided at any other suitable location where it may be used to facilitate the communication of electromagnetic energy propagating from second reflecting element 32. Input port 50 is coupled to integrator 28 and receives electromagnetic energy from second reflecting element 32. Input port 50 may be generally positioned so as to not interfere with the collection or transmission of electromagnetic energy. Input port 50 comprises an element defining a pathway for electromagnetic energy received from second reflecting element 32. Alternatively, input port 50 may be any other suitable appendage, conduit, element or object operable to facilitate the communications between second reflecting element 32 and target surface 15.

One or more detectors 52 operate to measure electromagnetic energy contained within integrator 28 according to one embodiment of the present invention. Detectors 52 may be mounted directly on the surface of integrator 28 or alternatively included within integrator 28. A series of detectors 52 may be mounted such that they are offset from each other, i.e., not necessarily 180° apart or on opposite sides of the integrating sphere. Detectors 52 may also communicate with a processor, as described in more detail below with reference to FIG. 4.

Integrator 28 may also include an additional input port 46 that receives electromagnetic energy reflected by first reflecting element 30, propagating through measurement port 16 and toward target surface 15. This communication is shown in greater detail in FIG. 3, where additional input port 46 is illustrated as providing a path for electromagnetic energy reflected by first reflecting element 30.

In operation, energy source 36 provides electromagnetic energy that is passed to chopper 40 where the electromagnetic energy may be apportioned in time between first reflecting element 30 and second reflecting element 32. According to the teachings of the present invention, a portion of electromagnetic energy passes from energy source 36, through the circulating discs of chopper 40, and to first reflecting element 30. This first portion of electromagnetic energy that is communicated to first reflecting element 30 may be focused or otherwise modified by lens 44 where appropriate. In addition, a second portion of electromagnetic energy is reflected by the rotating discs of chopper 40. The second portion of electromagnetic energy is communicated from energy source 36, to the reflective portion of the rotating discs of chopper 40, and then to second reflecting element 32. A third portion of electromagnetic energy is absorbed by the absorptive portion of the rotating discs of chopper 40.

First reflecting element 30 directs the electromagnetic energy that it receives toward target surface 15 via measurement port 16. This electromagnetic energy is directed at an angle that is near grazing or approximately parallel to target surface 15 to which a reflectance characteristic is sought to be determined. In an alternating fashion, first reflecting element 30 is reflecting electromagnetic energy toward target surface 15 while second reflecting element 32 passes electromagnetic energy toward target surface 15, via input port 50. Second reflecting element 32 passes electromagnetic energy toward target surface 15 from input port 50 at an angle that is approximately near normal to target surface 15 to which a reflectance characteristic is sought to be determined. The reflected electromagnetic energy from target surface 15 may be collected or otherwise received by integrator 28, which may be an integrating sphere, and be detected by one or more detectors 52. One or more detectors 52 may then operate to collect the data relating to all of the reflected electromagnetic energy from target surface 15 to a processor for example, as described in more detail below with reference to FIG. 4.

Figure 4:
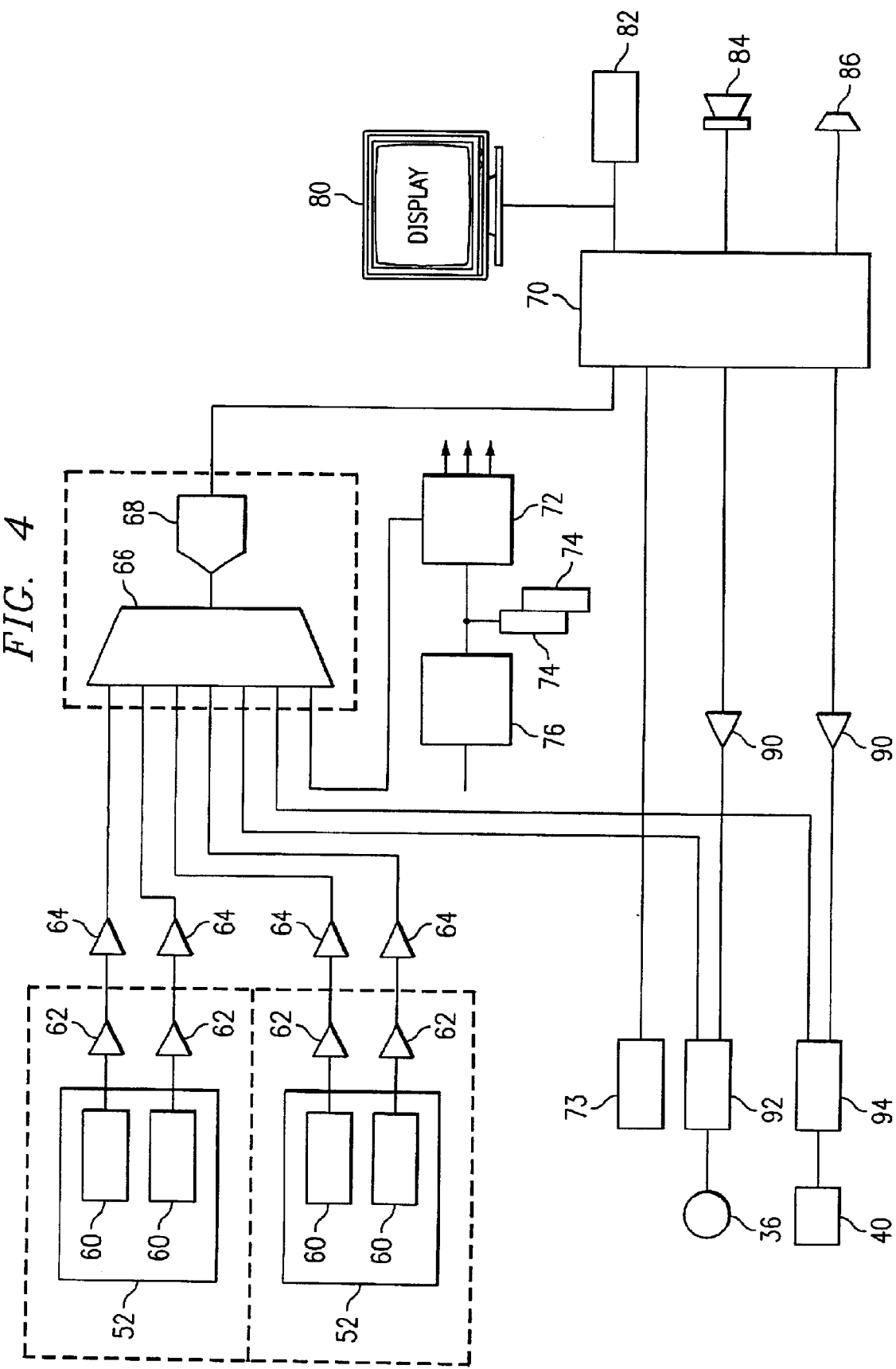
FIG. 4 is a block diagram of the reflectance determination system of FIG. 1 in accordance with one embodiment of the present invention.

FIG. 4 illustrates internal elements of reflectance determination system 10 according to one embodiment of the present invention. In this embodiment, reflectance determination system 10 includes a set of sensing elements 60, a set of pre-amplifiers 62, a set of variable gain amplifiers 64, a multiplexer 66 coupled to an analog-to-digital converter 68, and a processor 70. These components cooperate in order to receive and to evaluate electromagnetic energy that is reflected from target surface 15. In other embodiments one or more of these elements may be omitted, replaced and/or additional elements may be added.

One or more sensing elements 60 may be included within one or more detectors 52 as illustrated in FIG. 4. According to a particular embodiment of the present invention, two sensing elements 60 are provided within each detector 52. Sensing elements 60 operate to provide an optical-to-electrical conversion of electromagnetic energy received from target surface 15. Sensing elements 60 are pyro-electric detectors in one embodiment of the present invention, each of which may include an associated filter sensitive to a particular frequency band within the frequency spectrum. As used herein "each" means every one of at least a subset of the identified items. In a particular embodiment of the present invention, sensing elements 60 include a filter responsive to one of the frequency bands (stated in terms of wavelength) in the following ranges: 8–12 microns, 3–5 microns, 2.2 microns and above, and 1–14 microns. Alternatively, sensing elements 60 may include an associated filter that detects any frequency band in the frequency spectrum or sensing elements 60 may include any other element or object operable to distinguish or otherwise to detect electromagnetic energy.

Preamplifiers 62 are each coupled to respective sensing elements 60. Preamplifiers 62 amplify a signal received from one or more detectors 52, via one or more sensing elements 60. Alternatively, preamplifiers 62 may be eliminated or alternatively replaced with any component, object or element operable to modify, amplify or otherwise influence a signal or communication received from one or more detectors 52. One or more preamplifiers 62 are each coupled to and communicate with one or more variable gain amplifiers 64.

One or more various gain amplifiers 64 operate to receive an input signal from preamplifiers 62 and amplify the signal in order to provide data, having optimal signal strength, to multiplexer 66 and to analog to digital converter 68 in accordance with one embodiment of the present invention. One or more variable gain amplifiers 64 receive an electromagnetic energy signal from one or more preamplifiers 62 and determine whether or not the signal falls into a suitable range to be received by multiplexer 66. One or more variable gain amplifiers 64 may be set to an appropriate specific gain in order to enhance the accuracy of reflectance determination system 10. Variable gain amplifiers 64 may also provide a false detection element for one or more detectors 52 in eliminating received signals that do not fall within a specified input range. Variable gain amplifiers 64 provide an output measurement of electromagnetic energy for each frequency band associated with one or more sensing elements 60. Variable gain amplifiers 64 may operate to provide a signal measurement at one angle of incident for a single frequency band in the frequency spectrum as determined by an associated sensing element 60, and further output a signal measurement from the other angle of incident at the same frequency band. This information may then be decoded or otherwise processed by processor 70, which may then determine from which angle of incident the data is being sampled. One or more variable gain amplifiers 64 also recognize the repetitive cycle of passing electromagnetic energy, reflecting electromagnetic energy, and then absorbing electromagnetic energy. Where appropriate, one or more variable gain amplifiers 64 may be tuned or otherwise suitably adjusted by processor 70.

Multiplexer 66 receives a communication from one or more variable gain amplifiers 64 and multiplexes the data such that an output may be generated to analog to digital converter 68. Multiplexer 66 aggregates a series of inputs received from variable gain amplifiers 64 such that a single line of electromagnetic energy data is provided to analog-to-digital converter 68, potentially inclusive of a value of reflectance energy at each respective frequency. Multiplexer 66 may also receive one or more feedback signals as discussed below.

Analog to digital converter 68 receives a communication from multiplexer 66 and converts each analog signal to a digital signal that may be communicated to processor 70. Both multiplexer 66 and analog to digital converter 68 (along with reflectance determination system 10 generally) may be powered by a power source 72, which may be monitored by multiplexer 66 and analog to digital converter 68 for diagnostics or troubleshooting purposes, for example. Power source 72 may be a DC power supply or an AC power supply, and alternatively include elements such as one or more batteries 74 and a battery charger 76. Battery charger 76 may operate to provide power to reflectance determination system 10 while in operation, or alternatively charge while reflectance determination system 10 is not in operation. Reflectance determination system 10 may be otherwise powered by any other suitable power source or energy-generating element or device.

Processor 70 generally coordinates synchronous detection of reflectance properties of a target surface using data collected from multiple frequency bands. Processor 70 may include hardware and/or software operable to perform various tasks or sets of instructions, such as calibration for example, that facilitate a determination or measurement of a reflectance characteristic of an associated surface plane. Processor 70 may also include one or more algorithms that provide functions such as feedback or calibration to reflectance determination system 10.

In a particular embodiment of the present invention, processor 70 includes a microprocessor that receives the digitized signals from analog to digital converter 68. The digitized signals may then be stored in a memory and then processed to determine one or more reflectance values at each incident angle and wavelength band. The memory provided within, or alternatively coupled to, processor 70 may be any suitable memory storage unit, such as an erasable programmable read only memory (EPROM), an electrically erasable programmable read only memory (EEPROM), or a static random access memory (SRAM) for example, that stores data or information relating to one or more reflectance properties of a surface plane.

Processor 70 may provide the results of the determination of one or more reflectance properties of a surface (through a digital signal) to a display 80, such as a liquid crystal display (LCD) for example. Display 80 may be coupled to a keyboard 82 operable to control various parameters associated with reflectance determination system 10. Display 80 may be coupled to housing 12 (described in greater detail below) or provided as a component external to reflectance determination system 10. In addition, keyboard 82 may be provided on the exterior of housing 12 (described in greater detail below) or alternatively as a component external to reflectance determination system 10. Alternatively, the digital signal provided by processor 70 may be downloaded or otherwise communicated to a computer or any other device for additional processing or display. Other suitable user input and output interfaces may be used where appropriate according to particular needs.

A graphical user interface may be provided on the exterior of housing 12 of reflectance determination system 10, providing instant feedback to a user thereof. The graphical user interface may include a series of associated controls or buttons allowing a user of reflectance determination system 10 to control one or more parameters associated with determining a reflectance characteristic of a surface plane. The graphical user interface may also include guidance tools operable to facilitate the interaction between reflectance determination system 10 and a user of the system. In the case where an operator of reflectance determination system 10 is minimally trained, suitable software may be provided that indicates a "go" (operational) or "no-go" (non-operational) status signal to the operator. This software provides for operation of reflectance determination system 10 with minimal effort or knowledge associated with reflectance measurements and calculations.

Processor 70 may be coupled to an audio feedback 84 that signals to a user of reflectance determination system 10 that a measurement has been completed. Processor 70 may also be coupled to a communications port 86 that facilitates a link to a desktop computer operable to receive data and to troubleshoot reflectance determination system 10.

In addition, processor 70 may be coupled to one or more additional components operable to download information to, or receive information from, reflectance determination system 10 in order to enhance or otherwise facilitate the determination of a reflectance characteristic of a surface plane. This downloaded information may be customized for the particular surface or object to which a reflectance on an emissivity value is sought to be determined.

Processor 70 may also include a sleep timer element that is provided for reflectance determination system 10. The sleep timer element may automatically power-down reflectance determination system 10 after periods of non-use in order to conserve power or energy used to operate the instrument. In the case where the instrument is powered down, the data or information collected by reflectance determination system 10 may be stored in the memory of processor 70 and quickly retrieved once the instrument is powered up or resumes operation.

Processor 70 may determine the position of chopper 40 based on information received from analog to digital converter 68 in accordance with one embodiment of the present invention. Alternatively, a separate position sensor 73 may detect the position of chopper 40 and communicate such information to processor 70. Processor 70 may discern the angle of incident as well as evaluate the origin of a sample of electromagnetic energy, i.e. reflected by first reflecting element 30 or second reflecting element 32. The information provided by analog to digital converter 68 may reflect a number of samples (such as 128 for example) for both angles of incident, where these numbers are averaged repeatedly or otherwise manipulated to provide an accurate measurement of a reflectance characteristic or property associated with a surface plane.

Processor 70 may also include stored reference data from a previously-calibrated lab standard that provides a base-line reference point in calibrating reflectance determination system 10 and in calculating one or more reflectance properties. Thus, when reflectance determination system 10 is operational, processor 70 may implement a calibration routine that immediately determines the accuracy level of reflectance determination system 10 and may alter calibration parameters based on information or data included within the calibration routine. In a particular embodiment of the present invention, calibration of reflectance determination system 10 may be based on a black-box element having an emissivity of 1, i.e., the black-box element functions as both a good electromagnetic radiator and a good electromagnetic absorber. Reflectance characteristics or properties of target surface 15 to be evaluated may thus be compared to the black-box element (or base-line) to provide a reflectance percentage value, potentially to be displayed to a user of reflectance determination system 10. Generally, after a series of samples is taken from a target surface to which reflectance characteristics are sought, a series of algorithms process the information or otherwise average the numbers (discarding extraneous information where appropriate) resulting in a single number for each frequency band at each angle. The resultant eight numbers may then be presented at display 80, which reflect a reflectance percentage (normalized to 100%) in a graphical representation, for example.

Reflectance determination system 10 may also include a calibration-timing element to a user, which may be included within processor 70 for example, or alternatively within or coupled to any other suitable component within reflectance determination system 10. The timing element may operate to indicate that reflectance determination system 10 needs to be calibrated after some designated period of time. This would allow reflectance determination system 10 to be recalibrated periodically in order to yield results that are highly accurate. According to the teachings of one embodiment of the present invention, the accuracy of reflectance determination system 10 is approximately +/- 2%, with a repeatability (i.e. the same value consistently reported) value of approximately +/- 1%.

Processor 70 may also operate to provide an output to one or more amplifiers 90. One or more amplifiers 90 receive a signal from processor 70, amplify the signal, and communicate the signal to a source intensity controller 92 and to a chopper frequency controller 94. These components cooperate to provide a closed-loop control for energy source 36 and chopper 40. Source intensity controller 92 receives a signal from processor 70, via amplifier 90, and responds by adjusting energy source 36 accordingly (based on predetermined values that are stored in processor 70). Similarly, chopper frequency controller 94 receives a signal from processor 70, via amplifier 90, and adjusts chopper 40 accordingly by varying the voltage potential across chopper 40. Both source intensity controller 92 and chopper frequency controller 94 provide stability to reflectance determination system 10, and further provide feedback to multiplexer 66, such that variances in associated parameters may be made where appropriate. As illustrated in FIG. 4, source intensity controller 92 and chopper frequency controller 94 each provide an immediate feedback signal that is communicated to processor 70, via multiplexer 66 and analog to digital converter 68. Thus, processor 70 may count chopper cycles per unit of time for example, via chopper frequency controller 94, and adjust chopper 40 accordingly. Processor 70 may monitor energy source 36, via source intensity controller 92, and effect changes or variances of current through energy source 36 or motor 38.

Figure 5:
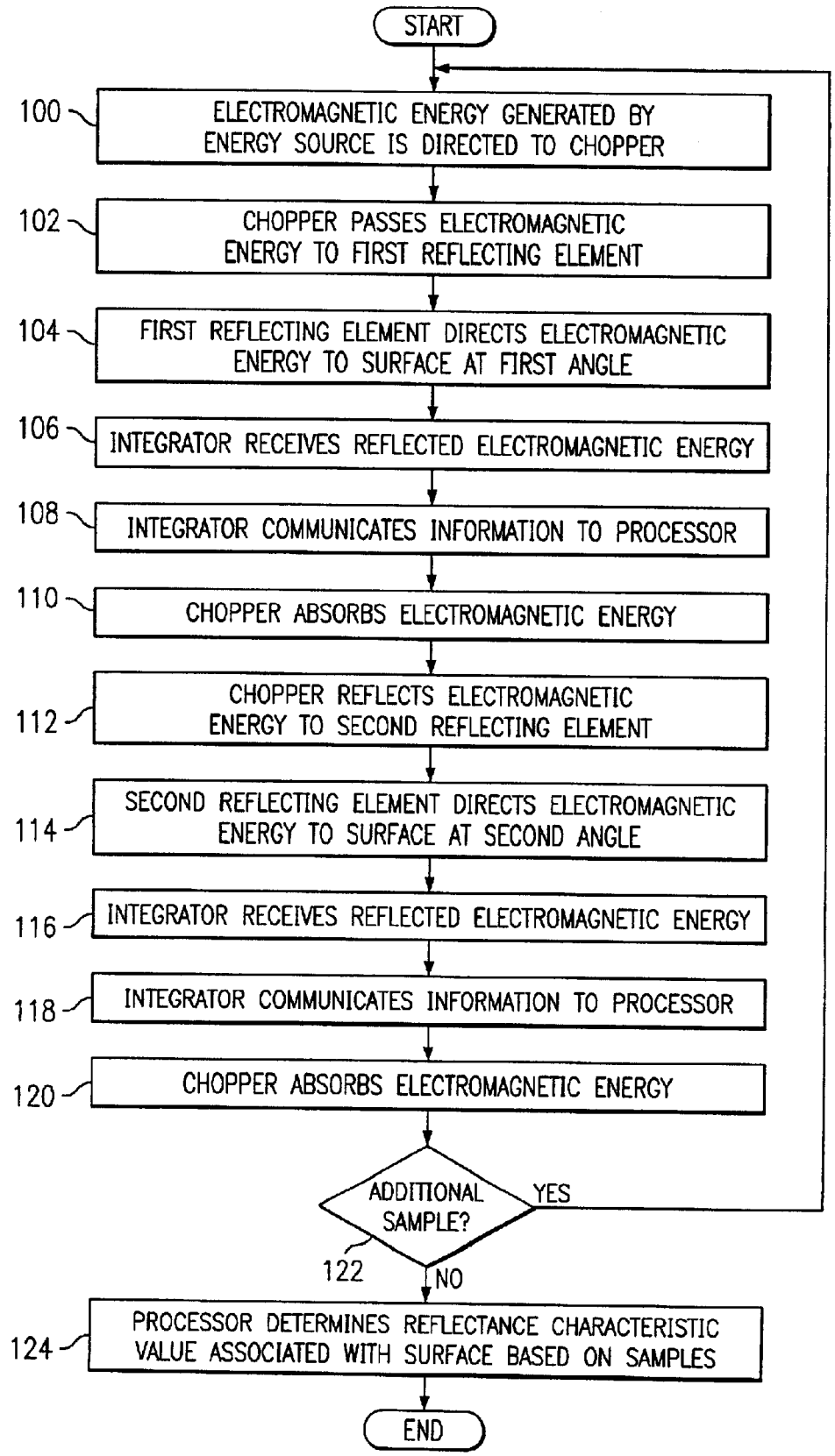
FIG. 5 is a flow chart illustrating a method for measuring reflectance characteristics of a surface in accordance with one embodiment of the present invention.

FIG. 5 illustrates a method for measuring reflectance properties of a target surface in accordance with one embodiment of the present invention. In this embodiment a single energy source, dual-angled reflectance measurement system is used. The method begins at a first step 100 where electromagnetic energy is generated by energy source 36 and directed to chopper 40 by alignment of energy source 36 with copper 40. At step 102, chopper 40 passes electromagnetic energy to first reflecting element 30, where first reflecting element 30 directs the electromagnetic energy at an angle near grazing (approximately parallel as described above) toward target surface 15 flush with measurement port 16. This direction of electromagnetic energy is illustrated generally at step 104.

Integrator 28 receives reflected electromagnetic energy from target surface 15 at step 106. At step 108, integrator 28 communicates this information to processor 70. Processor 70 may then begin computation of a reflectance characteristic associated with target surface 15 based on the data received from integrator 28. This data will then be synthesized later with information propagating from second reflecting element 32 toward target surface 15.

At step 110, chopper 40 absorbs electromagnetic energy provided by energy source 36. Generally, the absorptive section of rotating discs within chopper 40 provide a point of reference for a given reflectance characteristic to be measured by detectors 52. The calibration provides a noise-filtering function to reflectance determination system 10. At step 112, chopper 40 reflects electromagnetic energy to second reflecting element 32. Second reflecting element 32 directs electromagnetic energy to target surface 15 at a second angle that, in one embodiment of the present invention, is near normal (as described above) to target surface 15. At step 116, integrator 28 receives reflected electromagnetic energy from target surface 15. Integrator 28 communicates information to processor 70 at step 118 such that a reflectance characteristic may be determined that is based on the data reflected by target surface 15. At step 120, chopper 40 again absorbs electromagnetic energy and the cycle of chopper 40 repeats, i.e., pass, reflect, absorb electromagnetic energy.

At step 122, a determination is made if additional samples need to be taken or if the computational analysis performed by processor 70 is adequate to satisfy the initiated query for a reflectance characteristic calculation of target surface 15. If additional samples need to be taken, the steps of the flowchart illustrated in FIG. 5 may be repeated beginning at step 100, where electromagnetic energy generated by energy source 36 is directed to chopper 40. In the case where additional samples are not necessary to satisfy the measurement inquiry for target surface 15, at step 124 processor 70 may determine a reflectance characteristic value associated with the surface based on the already-collected samples. This information may then be displayed or otherwise communicated to a user of reflectance determination system 10.

Although the present invention has been described in detail with reference to particular embodiments as illustrated in FIGS. 1 through 5, it should be understood that various other changes, substitutions and alterations may be made hereto without departing from the spirit and scope of the present invention. For example, although the present invention has been described as inclusive of a single energy source 36, multiple energy sources may be provided in order to generate electromagnetic energy to be provided to chopper 40. In one embodiment in which multiple energy sources are provided, chopper 40 may be eliminated entirely. Alternatively, energy source 36 may be external to housing 12 such that electromagnetic energy is provided to chopper 40 via a structure or an element that is external to reflectance determination system 10.

Additionally, although the present invention has been described with reference to energy source 36 as providing infrared electromagnetic energy, various other types of energy, such as microwave, ultraviolet or visual, for example, is contemplated by the teachings of the present invention. Alternatively, any other suitable energies within the electromagnetic spectrum may be implemented where appropriate in order to collect data resulting in a reflectance characteristic being evaluated for a given surface plane.

Also, although first reflecting element 30 and second reflecting element 32 have been described as operative to receive portions of electromagnetic energy directed by chopper 40, a series of optical components or devices may be provided within housing 12 that operate to direct or otherwise influence the propagation of electromagnetic energy therein. Additionally, a series of optical components may be provided within or external to integrator 28 that operate to enhance, amplify, modify or otherwise influence the communication of electromagnetic energy within reflectance determination system 10.

Additionally, although reflectance determination system 10 has been described as being implemented to discern a reflectance characteristic of surfaces, devices, or components within the field of aeronautics, the present invention has applications to virtually any surface in which emissivity or reflectance characteristics are sought to be determined. The present invention may be used in space applications or in applications where properties of a surface may be determined by evaluating variations in surface properties. In addition, although reflectance determination system 10 has been described as portable, it may be stationary and mounted on any table, block, or element where appropriate and according to particular needs. Numerous other changes, substitutions, variations, alterations, and modifications may be suggested to one skilled in the art and it is intended that the present invention encompass all such changes, substitutions, variations, alterations, and modifications as falling within the spirit and scope of the appended claims.

What is claimed is:

1. A portable handheld apparatus for measuring properties of a surface, comprising:

an electromagnetic energy system operable to generate a first beam of electromagnetic energy exiting a port of the apparatus at an angle that is near normal to a surface plane and to generate a second beam of electromagnetic energy exiting the port at an angle that is near grazing to the surface plane;

an integrator operable to receive portions of the first and second beams of electromagnetic energy that are reflected at the surface plane; and a processor coupled to the integrator and operable to receive communication from the integrator associated with the reflected portions of the first and second beams of electromagnetic energy and to convert the communication to at least one reflectance characteristic value associated with the surface.

2. The portable apparatus of claim 1, further comprising one or more detectors coupled to the integrator and each operable to respond to a band of electromagnetic energy in the frequency spectrum, the detectors being further operable to communicate data associated with the portions of the first and second beams of electromagnetic energy to the processor.

3. The portable apparatus of claim 2, further comprising a first reflecting element and a second reflecting element operable to receive portions of the first and second beams of electromagnetic energy respectively, wherein the first reflecting element directs the portion of the first beam of electromagnetic energy that it receives toward the surface at an angle that is near normal to the surface plane, and wherein the second reflecting element directs the portion of the second beam of electromagnetic energy that it receives toward the surface at an angle that is near grazing to the surface plane.

4. The portable apparatus of claim 3, wherein the first and second reflecting elements are mirrors, and wherein the mirrors each comprise a gold surface.

5. The portable apparatus of claim 3, further comprising a multiplexer coupled to an analog to digital converter, the multiplexer operable to receive communication from one or more of the detectors via one or more variable gain amplifiers, wherein the analog-to-digital converter is coupled to the multiplexer and operable to receive information from the multiplexer associated with at least one reflectance characteristic of the surface and to communicate the information to the processor.

6. The portable apparatus of claim 1, further comprising a lens operable to receive and to focus portions of the first and second beams of electromagnetic energy generated by the electromagnetic energy system.

7. The portable apparatus of claim 1, wherein the processor receives one or more feedback signals from the analog to digital converter and responds to the feedback signals by modifying one or more parameters associated with the electromagnetic energy system.

8. The portable apparatus of claim 1, further comprising a display operable to receive and to display information communicated by the processor associated with the reflectance characteristic value of the surface.

9. The portable apparatus of claim 1, further comprising a battery charger operable to receive and to continuously charge a battery, wherein the battery is operable to provide power to the portable apparatus.

10. The portable apparatus of claim 1, wherein the electromagnetic energy system further comprises a chopper operable to execute a repetitive cycle in which electromagnetic energy that is generated by the electromagnetic energy system is directed by the chopper to a first reflecting element to generate the first beam of electromagnetic energy, then absorbed by the chopper, and then directed to a second reflecting element to generate the second beam of electromagnetic energy, and then absorbed by the chopper.

11. The portable apparatus of claim 10, wherein the processor is operable to receive data associated with the repetitive cycle, the processor being further operable to distinguish portions of the data which relate to the first and second beams of electromagnetic energy and the portions of the data associated with a frequency, at least some of the data being averaged in order to obtain at least one reflectance characteristic value associated with the surface.

12. The portable apparatus of claim 10, wherein the processor is operable to receive data associated with the number of cycles executed by the chopper and to generate at least one reflectance characteristic value associated with the surface that is based on the data.

13. The portable apparatus of claim 1, wherein the processor comprises software operable to guide a user of the portable apparatus through the operation thereof.

14. A method for determining one or more reflectance properties of a surface using a portable handheld apparatus, comprising:
reflecting a first beam of electromagnetic energy off of a measured surface, the first beam contacting the measured surface at an angle that is near normal to the measured surface;
reflecting a second beam of electromagnetic energy off of the measured surface, the second beam contacting the measured surface at an angle that is near grazing to the measured surface;
collecting reflected portions of the first and second beams of electromagnetic energy; and
determining at least one reflectance characteristic value associated with the measured surface based on the reflected portions of the first and second beams of electromagnetic energy.

15. The method of claim 14, further comprising generating the first and second beams of electromagnetic energy with a single electromagnetic energy source.

16. The method of claim 15, further comprising focussing portions of the first and second beams of electromagnetic energy generated by the electromagnetic energy system before the portions reach the measured surface.

17. The method of claim 16, further comprising modifying one or more parameters associated with the electromagnetic energy source based on one or more feedback signals.

18. The method of claim 14, further comprising displaying information at a graphical user interface that is associated with one or more reflectance characteristics of the measured surface.

19. The method of claim 14, further comprising charging a power source contained in the portable apparatus while the portable apparatus is in operation, the power source being operable to provide power to the portable apparatus.

20. The method of claim 14, further comprising generating the first and second beams of electromagnetic energy from a single electromagnetic energy source using a chopper.

21. The method of claim 14, further comprising executing a repetitive cycle in which electromagnetic energy is directed to a first reflecting element, then absorbed by an absorptive portion, and then directed to a second reflecting element.

22. The method of claim 21, further comprising:
receiving data associated with the repetitive cycle;
distinguishing portions of the data which relate to the first and second beams of electromagnetic energy and the portions of the data associated with a frequency band; and
averaging respectively the portions of data in order to obtain at least one reflectance characteristic value associated with the measured surface.

23. The method of claim 14, further comprising providing a series of instructions to guide a user of the portable apparatus through the operation thereof.

24. A system for determining one or more reflectance properties of a surface using a portable handheld apparatus, comprising:
means for reflecting a first beam of electromagnetic energy off of a measured surface, the first beam contacting the measured surface at an angle that is near normal to the measured surface;
means for reflecting a second beam of electromagnetic energy off of the measured surface, the second beam contacting the measured surface at an angle that is near grazing to the measured surface;
means for collecting reflected portions of the first and second beams of electromagnetic energy; and
means for determining at least one reflectance characteristic value associated with the measured surface based on the reflected portions of the first and second beams of electromagnetic energy.

25. The system of claim 24, further comprising means for generating the first and second beams of electromagnetic energy with a single electromagnetic energy source.

26. The system of claim 25, further comprising means for focussing portions of the first and second beams of electromagnetic energy generated by the electromagnetic energy system before the portions reach the measured surface.

27. The system of claim 26, further comprising means for modifying one or more parameters associated with the electromagnetic energy source based on one or more feedback signals.

28. The system of claim 24, further comprising means for displaying information at a graphical user interface that is associated with one or more reflectance characteristics of the measured surface.

29. The system of claim 24, further comprising means for charging a power source contained in the portable apparatus while the portable apparatus is in operation, the power source being operable to provide power to the portable apparatus.

30. The system of claim 24, further comprising means for generating the first and second beams of electromagnetic energy from a single electromagnetic energy source using a chopper.

31. The system of claim 24, further comprising means for executing a repetitive cycle in which electromagnetic energy is directed to a first reflecting element, then absorbed by an absorptive portion, and then directed to a second reflecting element.

32. The system of claim 31, further comprising:
means for receiving data associated with the repetitive cycle;
means for distinguishing portions of the data which relate to the first and second beams of electromagnetic energy and the portions of the data associated with a frequency band; and
means for averaging respectively the portions of data in order to obtain at least one reflectance characteristic value associated with the measured surface.

33. The system of claim 24, further comprising means for providing a series of instructions to guide a user of the portable apparatus through the operation thereof.

34. A portable handheld apparatus for measuring properties of a surface, comprising:
an electromagnetic energy system operable to generate a first beam of electromagnetic energy exiting a port of the apparatus at an angle that is near normal to a surface plane and to generate a second beam of electromagnetic energy exiting the port at an angle that is near grazing to the surface plane;
an integrator operable to receive portions of the first and second beams of electromagnetic energy that are reflected at the surface plane;
a processor coupled to the integrator and operable to receive communication from the integrator associated with the reflected portions of the first and second beams of electromagnetic energy and to convert the communication to at least one reflectance characteristic value associated with the surface;
a first reflecting element and a second reflecting element operable to receive portions of the first and second beams of electromagnetic energy respectively, wherein the first reflecting element directs the portion of the first beam of electromagnetic energy that it receives toward the surface at an angle that is near normal to the surface plane, and wherein the second reflecting element directs the portion of the second beam of electromagnetic energy that it receives toward the surface at an angle that is near grazing to the surface plane;
a chopper operable to execute a repetitive cycle in which electromagnetic energy that is generated by the electromagnetic energy system is directed to the first reflecting element, then absorbed by the chopper, and then directed to the second reflecting element, and then absorbed by the chopper;
one or more detectors coupled to the integrator and each operable to respond to a band of electromagnetic energy in the frequency spectrum, the detectors being further operable to communicate data associated with the portions of the first and second beams of electromagnetic energy to the processor; and
a display operable to receive and to display information communicated by the processor associated with the reflectance characteristic value of the surface.

35. A method for determining one or more reflectance properties of a surface using a portable handheld apparatus, comprising:
generating a first beam of electromagnetic energy that propagates toward a surface plane at an angle that is near normal to the surface plane;
generating a second beam of electromagnetic energy that propagates toward the surface plane at an angle that is near grazing to the surface plane;
receiving portions of the first and second beams of electromagnetic energy that are reflected at the surface plane;
receiving the reflected portions of the first and second beams of electromagnetic energy;
providing one or more detectors operable to respond to a frequency band of electromagnetic energy in the frequency spectrum;
receiving an electromagnetic signal from one or more of the detectors via one or more variable gain amplifiers, the signal being associated with the reflected portions of the first and second beams of electromagnetic energy;
multiplexing the electromagnetic signal;
transmitting the electromagnetic signal to an analog to digital converter;
converting the electromagnetic signal from an analog format to a digital format; and
communicating the electromagnetic signal to a processor such that at least one reflectance characteristic of the surface plane may be determined.

36. An electromagnetic energy controller for a portable handheld measuring apparatus, comprising:
a chopper operable to transmit a first portion of electromagnetic energy toward a first reflecting element and to reflect a second portion of electromagnetic energy toward a second reflecting element and to absorb a third portion of electromagnetic energy, whereby the chopper executes a repetitive cycle in which the chopper transmits, reflects, and then absorbs portions of electromagnetic energy, wherein the first and second portions of electromagnetic energy are reflected by the first and second reflecting elements respectively toward a surface plane; and
a motor operable to effect motion of the chopper.

37. The apparatus of claim 36, further comprising an electromagnetic energy source operable to generate electromagnetic energy that propagates toward the chopper.

38. The apparatus of claim 36, wherein the chopper comprises two rotating discs, each of the rotating discs including sections operable to facilitate the execution of the repetitive cycle.

39. The apparatus of claim 38, wherein part of at least one of the discs comprises a reflective portion that comprises gold-plated aluminum.

40. The apparatus of claim 39, wherein part of at least one of the discs comprises an absorptive portion that comprises aluminum that includes a coating of absorbent paint operable to absorb electromagnetic energy.

41. The apparatus of claim 40, wherein part of at least one of the discs comprises an outer portion defining a cavity therethrough operable to transmit electromagnetic energy substantially unaffected.

42. The apparatus of claim 41, further comprising a processor operable to tune the chopper in response to receiving one or more feedback signals associated with one or more parameters of the chopper.

43. The apparatus of claim 36, further comprising a display operable to receive and to display information associated with the electromagnetic energy reflected at the surface plane.

44. The apparatus of claim 36, further comprising a lens operable to receive and to focus electromagnetic energy received from the chopper.

45. The apparatus of claim 36, wherein the first and second reflecting elements are each mirrors that comprise gold.

46. The apparatus of claim 36, further comprising a battery charger operable to receive and to continuously charge a battery, wherein the battery is operable to provide power to the motor.

47. A method for generating and influencing electromagnetic energy using a portable handheld apparatus, comprising:
   transmitting a first portion of electromagnetic energy toward a first reflecting element;
   reflecting a second portion of electromagnetic energy toward a second reflecting element;
   absorbing a third portion of electromagnetic energy;
   executing a repetitive cycle with a chopper, the repetitive cycle comprising the preceding steps of transmitting, reflecting, and absorbing portions of electromagnetic energy, wherein the first and second portions of electromagnetic energy are reflected by the first and second reflecting elements respectively toward a surface plane; and
   receiving reflected electromagnetic energy from the surface plane.

48. The method of claim 47, further comprising generating electromagnetic energy that propagates toward the chopper.

49. The method of claim 47, wherein the chopper comprises two rotating discs, each of the rotating discs including sections operable to facilitate the execution of the repetitive cycle.

50. The method of claim 49, wherein part of at least one of the discs comprises a reflective portion that comprises gold-plated aluminum.

51. The method of claim 50, wherein part of at least one of the discs comprises an absorptive portion that comprises aluminum that includes a coating of absorbent paint operable to absorb electromagnetic energy.

52. The method of claim 51, further comprising transmitting electromagnetic energy substantially unaffected through at least one of the discs having an outer portion defining a cavity therethrough.

53. The method of claim 52, further comprising tuning the chopper in response to receiving one or more feedback signals associated with one or more parameters of the chopper.

54. The method of claim 47, further comprising displaying information associated with the electromagnetic energy reflected at the surface plane.

55. The method of claim 47, further comprising focusing electromagnetic energy received from the chopper.

56. The method of claim 47, further comprising: effecting motion of the chopper with a motor; and charging a power source operable to provide power to the motor.

57. A system for generating and influencing electromagnetic energy using a portable handheld apparatus, comprising:
   means for transmitting a first portion of electromagnetic energy toward a first reflecting element;
   means for reflecting a second portion of electromagnetic energy toward a second reflecting element;
   means for absorbing a third portion of electromagnetic energy;
   means for executing a repetitive cycle with a chopper, the repetitive cycle comprising the preceding steps of transmitting, reflecting, and absorbing portions of electromagnetic energy, wherein the first and second portions of electromagnetic energy are reflected by the first and second reflecting elements respectively toward a surface plane; and
   means for receiving reflected electromagnetic energy from the surface plane.

58. The system of claim 57, further comprising means for generating electromagnetic energy that propagates toward the chopper.

59. The system of claim 57, wherein the chopper comprises two rotating discs, each of the rotating discs including sections operable to facilitate the execution of the repetitive cycle.

60. The system of claim 59, wherein part of at least one of the discs comprises a reflective portion that comprises gold-plated aluminum.

61. The system of claim 60, wherein part of at least one of the discs comprises an absorptive portion that comprises aluminum that includes a coating of absorbent paint operable to absorb electromagnetic energy.

62. The system of claim 61, further comprising means for transmitting electromagnetic energy substantially unaffected through at least one of the discs having an outer portion defining a cavity therethrough.

63. The system of claim 62, further comprising means for tuning the chopper in response to receiving one or more feedback signals associated with one or more parameters of the chopper.

64. The system of claim 57, further comprising means for displaying information associated with the electromagnetic energy reflected at the surface plane.

65. The system of claim 57, further comprising means for focusing electromagnetic energy received from the chopper.

66. The system of claim 57, further comprising:
   means for effecting motion of the chopper with a motor; and
   means for charging a power source operable to provide power to the motor.

67. An electromagnetic energy controller for a portable handheld measuring apparatus, comprising:
   a chopper operable to transmit a first portion of electromagnetic energy toward a first reflecting element and to reflect a second portion of electromagnetic energy toward a second reflecting element and to absorb a third portion of electromagnetic energy, whereby the chopper executes a repetitive cycle in which the chopper transmits, reflects, and then absorbs portions of electromagnetic energy, wherein the first and second portions of electromagnetic energy are reflected by the first and second reflecting elements respectively toward a surface plane;
   a motor operable to effect motion of the chopper;

an electromagnetic energy source operable to generate electromagnetic energy that propagates toward the chopper;

a display operable to receive and to display information associated with the electromagnetic energy reflected at the surface plane; and a battery charger operable to receive and to continuously charge a battery, wherein the battery is operable to provide power to the motor.

68. A method for generating and influencing electromagnetic energy using a portable handheld apparatus, comprising:

generating electromagnetic energy that propagates toward a chopper;

transmitting a first portion of the electromagnetic energy toward a first reflecting element;

reflecting a second portion of the electromagnetic energy toward a second reflecting element;

absorbing a third portion of the electromagnetic energy;

executing a repetitive cycle with a chopper, the repetitive cycle comprising the preceding steps of transmitting, reflecting, and absorbing portions of electromagnetic energy, wherein the first and second portions of electromagnetic energy are reflected by the first and second reflecting elements respectively toward a surface plane;

receiving reflected electromagnetic energy from the surface plane;

tuning the chopper in response to receiving one or more feedback signals associated with one or more parameters of the chopper; and displaying information associated with the electromagnetic energy reflected at the surface plane.

* * * * *